United States Patent [19]

Marecki et al.

[11] Patent Number: 4,461,772

[45] Date of Patent: Jul. 24, 1984

[54] ADDITIVES FOR IMPROVING RUMINANT FEED UTILIZATION

[75] Inventors: Paul E. Marecki, Painesville; John M. Weaver, Mentor, both of Ohio

[73] Assignee: SDS Biotech Corporation, Painesville, Ohio

[21] Appl. No.: 477,236

[22] Filed: Mar. 21, 1983

Related U.S. Application Data

[62] Division of Ser. No. 185,171, Sep. 8, 1980, Pat. No. 4,423,224.

[51] Int. Cl.³ .................. A61K 31/41; A61K 31/275
[52] U.S. Cl. .................................... 424/269; 424/304
[58] Field of Search .............................. 424/269, 304

[56] References Cited

PUBLICATIONS

Kitaeva et al., Chem. Abst., vol. 92 (1980), p. 110933p.

*Primary Examiner*—Sam Rosen
*Attorney, Agent, or Firm*—John P. Hazzard

[57] ABSTRACT

At least one compound defined by one of the following formulae:

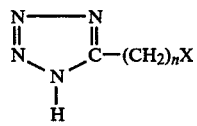

I.

where X represents Cl, Br,

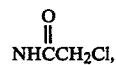

$NHSO_2CH_3$,

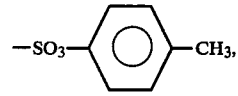

or $-SCH_3$, and n is 1 or 2; and $CH_3SO_2NHCH_2CH_2CN$ (II)

have been administered to animals to improve the efficiency of food utilization by these animals. These compounds can be administered orally by combining the compounds with feed compositions and fed to animals such as ruminants with a developed rumen function as well as other animals that ferment fibrous material and vegetable matter in the cecum or colon. These compounds effect the rumen metabolism to increase the production of propionate relative to other volatile fatty acids, particularly acetate and to inhibit methanogenesis.

20 Claims, No Drawings

ADDITIVES FOR IMPROVING RUMINANT FEED UTILIZATION

This application is a divisional application of U.S. Ser. No. 185,171 filed Sept. 8, 1980 now U.S. Pat. No. 4,423,224 issued Dec. 27, 1983.

BACKGROUND OF THE INVENTION

(1) Field of the Invention

This invention relates to novel compounds and methods for increasing the efficiency of feed utilization in animals, particularly ruminant animals.

More specifically, this invention relates to feed additives for ruminant feed compositions which alter rumen metabolism to result in inhibition of methane production and an increase in propionate production relative to acetate.

(2) State of the Art

The improvement of feed efficiency of ruminant animals has for many years been a highly desirable commercial objective. The economic incentive is clear. If a method is devised for increasing feed efficiency and/or the rate of weight gain of cattle or sheep while decreasing the amount of feed consumed by these animals, then the farmers' costs for raising these animals are reduced.

In order to improve the efficiency of feed utilization by ruminants, first it was necessary to discover and understand the mechanism by which these ruminants digest the various components of their feed and to determine the resultant digestion products which are metabolically utilized by the animal. As a result of extensive work in this area, the mechanism for carbohydrate utilization by ruminant animals is well known and documented in the literature. Raun in his U.S. Pat. Nos. 3,790,667, 3,790,668, 3,794,732 and 3,839,557, the disclosures of same are herein incorporated by reference, clearly sets out what is recognized as the accepted mechanism for the utilization of the feed carbohydrates by ruminant animals and further discloses the relevant references teaching the early work conducted in this area of technology. Raun found that propionate production could be increased and in turn improve ruminant feed utilization by orally administering to the ruminants selected polyether antibiotics and such physiologically-acceptable compounds, as thiostrepton, monensin and dianemycin. It is also pointed out in the Raun patents that inducing an increase in propionate production in the rumen of the animal results in a secondary benefit apart from the increase in feed utilization efficiency. The secondary benefit being the inhibition of ketosis which is the result of a high proportion of acetate in the rumen and which amounts to a clinical illness in the animal.

Since Raun's work, further studies have been conducted investigating the effect of monensin, in particular, on rumen metabolism, e.g., Van Nevel, et al, *Appld. and Envl. Microbio.*, 34(3), pgs. 251–257 (Sept. 1977) and Slyter, *Appld. and Envl. Microbio.*, 37(2), pgs. 283–288 (Feb. 1979). In addition, others have found that such additives as polyhalohemiacetal derivatives of saccharides and polysaccharides, Parish, et al, U.S. Pat. No. 3,615,649 and polyhaloalkamines, Parish, et al, U.S. Pat. No. 3,733,417, can improve the feed efficiency of ruminant animals. None of these feed additives, however, have proven to achieve the optimum results with respect to preventing the animal from reducing feed intake while at the same time inducing the optimal increase in propionate production in the rumen of these animals over an extended period of time.

SUMMARY OF THE INVENTION

It has now been discovered, in accordance with the present invention, a novel method for regulating rumen metabolism over an extended period of time.

Further in accordance with the present invention, novel compounds have been prepared utilizing an efficient mode of preparation.

Still further in accordance with the invention, specific 5-substituted tetrazoles and a precursor demonstrate the ability to regulate the metabolism of rumen microorganisms. More specifically, these compounds are shown to effect the inhibition of methanogenesis, to increase rumen propionate concentration, to decrease the rumen acetate concentration and to increase fermenation efficiency in ruminant animals.

These and other aspects of the invention will become clear to those skilled in the art upon the reading and understanding of the specification.

DESCRIPTION OF THE PREFERRED EMBODIMENTS

It has been recognized for several years that if methanogenesis could be partially or totally inhibited with a corresponding increase in propionate production in the rumen, the result would be that approximately 8 percent of the feed energy which is normally lost (ultimately through eructation) would be made available to the growing animal, see, for example, Hungate, *The Rumen And Its Microbes*, Academic Press, N.Y. (1966), pp. 246 and 247. Diversion of this energy loss from methanogenesis would in turn make this energy available for more productive metabolic processes such as the biosynthesis of propionate which is a major source of metabolic energy. The overall result for the animal might be expressed as improvement of feed efficiency and increased rate of weight gain. Thus, discovering the means for the metabolic regulation of methanogenesis would be a productive approach to ultimately improving the efficiency of feed utilization for ruminant animals.

It was found through extensive in vitro and in vivo studies that specific 5-substituted tetrazoles of formula I below and a precursor compound of formula II below, demonstrated the ability to inhibit methanogenesis and increase propionate production relative to acetate in the rumen of the animals.

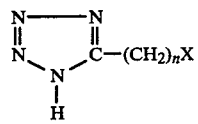
(I)

where X is —Cl, —Br,

—NHSO$_2$CH$_3$,

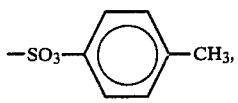

or —SCH₃, and n is 1 or 2; and

CNCH₂CH₂NHSO₂CH₃          (II)

The 5-substituted tetrazoles of the present invention are prepared by direct, efficient and high yield synthetic techniques, this being one of the advantages of the compounds of the present invention over other compounds disclosed in the prior art. The 5-substituted tetrazoles of this invention are generally prepared according to the following scheme:

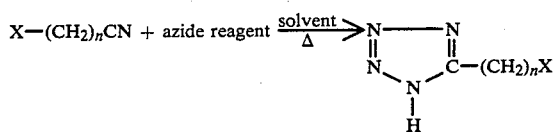

where X and n are the same as previously defined herein.

The different azide reagents which can be used are (1) NaN₃+NH₄Cl in DMF as disclosed in U.S. Pat. No. 2,977,372; (2) AlCl₃+NaN₃ in THF as disclosed in J.O.C., 34(4), (1969) 1141–1142; and (3) (n-Bu)₃SnN₃ in toluene as disclosed in J. Organomet. Chem., 33 (1971) 337–346. The selection of the particular azide reagent will be dependent upon the reaction conditions required to prepare the specific 5-substituted tetrazole, cost, availability of materials as well as other such considerations. It has been found, however, that while all of these reagents generally lead to the desired products, reagent (1) suffers from the difficulty of complete removal of DMF; reagent (2) was found to be useful in the preparation of water insoluble tetrazoles; while reagent (3) was found to be useful in preparing tetrazoles which required mild reaction conditions such as the chloroacetamido species. The alkylene nitrile reactants or precursors for the preparation of the 5-substituted tetrazoles of the present invention can be purchased through most bulk chemical suppliers. The particular procedure followed for preparing the 5-substituted tetrazoles of the present invention comprised heating the mixture of reactants and the selected azide reagent in the selected solvent for a period of time at reflux. While the actual reaction time is not critical, it was found the best results were achieved if the reaction took place for a minimum of 12 hours. Specific preparative procedures for compounds within the scope of this invention will be further illustrated in the examples that follow this discussion.

The in vitro as well as the in vivo studies conducted show the compounds of the present invention to be effective for inhibiting methane production by ruminant animals as well as increasing the relative propionate concentration in the rumen. It was also discovered that while the compounds of this invention were quite effective for the disclosed utility, their effectiveness can be enhanced by mixing the compounds of this invention with other known rumen metabolic regulators, e.g., polyether antibiotics (monensin, etc.). The relative amounts of these compounds administered were not found to be critical except as is evident, the amounts must be kept below toxic levels.

Various features and aspects of the present invention will be further illustrated in the examples that follow. While these examples will show one skilled in the art how to operate within the scope of this invention, they are not to serve as a limitation on the scope of the invention where such scope is only defined in the claims.

COMPOUND PREPARATION

The following examples will serve to illustrate the synthesis of the compounds within the scope of this invention.

EXAMPLE 1

Preparation of 5-(2-Chloroethyl)Tetrazole

A mixture of 39.9 g (0.3 mol) of AlCl₃, 600 mL of THF, and 86.78 g (1.33 mol) of NaN₃ and 26.86 g (0.3 mol) of ClCH₂CH₂CN were stirred and heated to reflux under Argon for 24 hours then cooled and acidified with 450 ml of 15 percent HCl solution. The resulting mixture was warmed on a steam bath to remove HN₃. The phases were then separated and the aqueous phase was extracted twice with 150 mL portions of ethyl acetate. The organic phases were combined, washed with saturated NaCl solution followed by drying over anhydrous Na₂SO₄. Removal of the solvent under reduced pressure gave 33.87 g of a brown solid, m.p. 88°–102.5° C. Three recrystallizations from ClCH₂CH₂Cl gave 23.55 g (59 percent) of desired compound as fine beige needles, m.p. 104°–105° C.

EXAMPLE 2

Preparation of 5-Chloromethyltetrazole

To a mixture of 26.6 g (0.2 mol) of AlCl₃ and 450 mL dry THF was added with stirring and in one portion, 57.2 g (0.88 mol) of NaN₃. The resulting mixture was stirred under Argon at room temperature for 15 minutes followed by the addition of 15.1 g (0.2 mol) of ClCH₂CN. The resulting mixture was heated and stirred at reflux for 24 hours then quenched with 300 mL of 15 percent HCl solution. The resulting 2-phase mixture was heated on a steam bath for 15 minutes to remove HN₃ after which the phases were separated. The aqueous phase was washed 3 times with 100 mL portions of ethyl acetate and then dried over anhydrous Na₂SO₄. Removal of the solvent under reduced pressure gave 26.07 g of black wax which was dissolved in 25 mL of H₂O. The resulting solution was adjusted to a pH 10 with NaOH. The aqueous alkaline solution was extracted 3 times with 100 mL portions of ether. The aqueous phase was then adjusted to pH 2 with 15 percent HCl solution. The aqueous phase was saturated with NaCl then extracted 3 times with 100 mL of ethyl acetate. The ethyl acetate phases were combined, washed with brine and then dried over anhydrous Na₂SO₄. Removal of solvent under reduced pressure gave 17 g of brown solid which was recrystallized from ClCH₂CH₂Cl to give 9.74 g of a brown solid, m.p. 72°–79° C. This brown solid was in turn recrystallized from CHCl₃ to give 5.33 g of the desired compound, m.p. 88.5–90.5. The mother liquor afforded an additional 0.98 g of the desired compound, m.p. 87°–88° C.

EXAMPLE 3

Preparation of
2-chloro-N-(2(1H-Tetrazol-5-yl)ethyl)acetamide

A solution of 9.3 g (65 mmols) of

and 32.37 g (97.5 m mols) of (n-Bu)$_3$SnN$_3$ in 150 mL of toluene was stirred and heated at reflux for 19 hours then cooled to room temperature. The supernatant liquid was decanted from the brown oil which formed. Removal of the solvent under reduced pressure gave a cloudy oil-solid mixture. The material was vigorously stirred with 300 mL of ether while anhydrous HCl gas was passed through the mixture resulting in a wax. The ether was decanted after which the wax was dissolved in 300 mL of hot ethyl acetate and anhydrous HCl gas was passed through the resulting solution. The solution became cloudy and an oil formed. The supernatant was separated from the oil and the solvent was removed from the supernatant under reduced pressure to give 2.61 g of an oily solid. This material was washed by stirring with ether then filtered to give 1.86 g of beige solid, m.p. 105°–120° C. Three recrystallizations of this material from absolute ethanol afforded 0.658 g of the desired compound as colorless to white nodules, m.p. 132°–133.5° C.

EXAMPLE 4

Preparation of
4-methyl-N-(2-(1H-Tetrazol-5-yl)ethyl)benzenesulfonate

A solution of 11.26 g (50 mmols) of

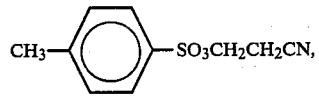

19.92 g (60 mmols) of (n-Bu)$_3$SnN$_3$, and 150 mL of dry THF was stirred and heated at reflux for 24 hours then cooled to room temperature. Removal of the solvent under reduced pressure gave a clear pale yellow oil which was stirred at room temperature for 30 minutes with 350 mL of ethereal HCl solution. The resulting mixture was filtered followed by washing the solid by stirring for 2 hours with 200 mL of ether to give 4.03 g of white powder, m.p. 150.5°–152.5° C. Recrystallization from 135 mL of boiling ethyl acetate afforded 2.98 g of the desired compound as colorless needles, m.p. 158°–159° C.

All the 5-substituted tetrazoles within the scope of this invention are prepared by the procedures illustrated in the previous examples. As indicated previously, the preparation of these compounds is direct and efficient, giving good yields of the desired compound.

IN VITRO STUDIES

A. Procedure

Below is set forth the procedure followed for testing the compounds of the present invention in vitro. For these studies, rumen fistulated sheep were fed a concentrate diet which constituted 3 parts chopped corn and cob and 1 part alfalfa pellets.

1. Rumen fluid was removed from a fistulated sheep and strained through 4 layers of cheese cloth to remove large feed particles.
2. One part rumen fluid was added to 3 parts of modified McDougal's Artificial Saliva, the pH was adjusted to 7.0 and the saliva solution was prewarmed to 39° C. in a water bath and gassed with $CO_2$.

(a) Modified McDougal Artificial Saliva composition:

| Salt | mmoles |
|---|---|
| NaHCO$_3$ | 58.5 |
| KHCO$_3$ | 58.5 |
| NaH$_2$PO$_4$ | 13.0 |
| KH$_2$PO$_4$ | 13.0 |
| NaCl | 8.0 |
| KCl | 8.0 |
| MgCl$_2$ | 0.3 |
| CaCl$_2$ | 0.2 |
| 100X salt solution Salt | g/L H$_2$O |
| NaCl | 47 |
| MgCl$_2$ | 6 |
| KCl | 57 |
| CaCl$_2$ | 4 |

To prepare (a), (i) 9.8 g NaHCO$_3$, 11.7 g KHCO$_3$, 5.1 g NaH$_2$PO$_4$ and 4.08 g KH$_2$PO$_4$ were diluted with two (2) liters of distilled H$_2$O; (ii) 20 mL of 100X salt solution was diluted to 1.33 l with tap H$_2$O; and (iii) mix (i) with (ii) to prepare the modified McDougal Artificial Saliva.

3. Add 0.01 g concentrate feed/1 mL of buffered rumen fluid (the buffered rumen fluid with concentrate should be stirred at all times to prevent the concentrate from settling).
4. Dispense 20 mL of buffered rumen fluid into 30 mL serum bottles that are being gassed with $CO_2$. (A manifold that gases 12 bottles at a time was used.) The bottles should be in a 39° C. H$_2$O bath.
5. The test compounds, i.e., the compounds of the present invention, were first added to the bottles. After the addition of the buffered rumen fluid to all 12 bottles, the gassing cannulae were quickly removed and a butyl rubber stopper was inserted in each bottle. An aluminum seal was then placed on each bottle and crimped tight. Note: do not remove the bottle from the water bath until it has been crimped.
6. The sealed bottles were removed from the water bath, shaken and placed in a 39° C. incubator for 18 hours.
7. After the 18-hour incubation, the bottles were removed from the incubator and the head space gas was analyzed using a gas partitioner.
8. Four mL of rumen fluid was removed from each bottle for volatile fatty acid (VFA) analysis.

(a) The 4 mL sample was added to a centrifuge tube to which had previously been added 0.04 mL of 50 percent H$_2$SO$_4$ and 1 mL 2-ethylbutyric acid (concentration 2 mL of 2-ethylbutyric acid/500 mL H$_2$O v/v).
(b) The mixture from (a) was centrifuged at 10000 xg for 20 minutes.
(c) The supernatant was removed and analyzed by gas-liquid chromatography. The above procedures were followed in all trials for testing the compounds of the present invention.

B. Results

The results of the in vitro tests are set out in Table I. It is pointed out that these results are reported in terms of relative concentration of the volatile fatty acids (VFA) acetate, propionate, and butyrate and percent methane inhibition to a negative control.

TABLE I

| | | Ratio Treated to Control | | | | |
|---|---|---|---|---|---|---|
| Compound | Levels ppm | $C_2^2$ | $C_3^2$ | $C_4^2$ | Total VFA | Methane Inhibition (%) |
| [1]T—$CH_2Cl$ | 50.0 | 0.74 | 1.49 | 0.95 | 0.96 | 96.8 |
| T—$CH_2CH_2Cl$ | 50.0 | 0.76 | 1.48 | 0.92 | 1.03 | 74.6 |
| T—$CH_2CH_2Br$ | 50.0 | 0.73 | 1.44 | 1.25 | 0.91 | 91.3 |
| T—$CH_2CH_2NHCCH_2Cl$ (O double bond on C) | 50.00 | 0.91 | 1.16 | 1.05 | 1.02 | 4.9 |
| T—$CH_2CH_2NHSO_2CH_3$ | 50.0 | 0.99 | 1.04 | 0.99 | 1.02 | 0.7 |
| T—$CH_2CH_2SO_3$—⟨phenyl⟩—$CH_3$ | 50.0 | 0.92 | 1.23 | 0.95 | 1.07 | 8.0 |
| $CNCH_2CH_2NHSO_2CH_3$ | 50.0 | 0.7 | 1.58 | 1.13 | 0.97 | 73.4 |

[1]T represents the tetrazole ring:
$$\begin{array}{c} N\!=\!\!=\!\!N \\ \| \quad \| \\ N \quad C- \\ \diagdown N \diagup \\ | \\ H \end{array}$$
in all cases.

[2]$C_2$ represents acetate, $C_3$ represents propionate and $C_4$ represents butyrate.

The results of the in vitro testing confirm that the compounds of the present invention are effective for increasing propionate production relative to acetate in rumen fluid as well as inhibiting the production of methane.

IN VIVO STUDIES

The in vitro studies showed the compounds of the present invention had the desired effect on the biochemistry of the rumen bacteria, however, it had yet to be determined whether or not this effect would be sustained in the animal where numerous other biochemical processes are simultaneously occuring.

A. Procedure and Treatments

Eight rumen fistulated sheep were used as test animals. Two sheep were alotted to each of three treatments and a control for each test. Group I was always the control group in each of the different trials. Groups II through IV had varying concentrations of compounds of the present invention added to the animals' feed. The feed ration in each trial constituted 3 parts chopped corn and cob and 1 part alfalfa pellets. Each sheep was offered 800 g daily of the feed in two equal portions. The particular compound and vitamin premix were mixed with chopped corn and cob. Any feed refusals were weighed back before each feeding and discarded. To prevent any mold growth, the feed was stored under refrigeration.

All animals in the various treatment groups were sampled for VFA's twice a week. Equal volumes of rumen fluid from each animal within a treatment were pooled for treatment VFA analysis. Fluid from individual animals was also analyzed for VFA. Individual animal VFA's within a treatment were averaged. This value was then averaged with pooled treatment VFA yielding the final treatment VFA value. All ratios and statistics were calculated using this final value. VFA's were calculated as the ratio treated to its respective pretreatment value. Each of the trials lasted for 90 days.

B. Results

Using the procedures set out in A, the data reported in Tables II and III were collected from trials using two of the compounds of the present invention.

TABLE II

Compound: 5-Chloromethyltetrazole

| | | Ratio of Treatment VFA to Pretreatment VFA | | | |
|---|---|---|---|---|---|
| Groups | Level[1] % | $C_2^2$ | $C_3^2$ | $C_4^2$ | Total VFA |
| I | Control | 1.02[3] | 0.99 | 0.90 | 0.87 |
| II | 0.01 | 1.01 | 0.98 | 1.02 | 0.96 |
| III | 0.05 | 0.97 | 1.05 | 1.04 | 0.88 |
| IV | 0.025 | 0.96 | 1.10 | 1.05 | 0.93 |

[1]Level is reported as percent of compound added to total amount of feed administered to the animal. A dose level of 0.05 corresponds to approximately 60 ppm of the compound in the rumen.
[2]$C_2$ represents acetate, $C_3$ represents propionate and $C_4$ represents butyrate.
[3]Average of all values for biweekly samples taken over the 90-day trial period.

TABLE III

Compound: 5-(2-Chloroethyl)Tetrazole

| | | Ratio of Treatment VFA to Pretreatment VFA | | | |
|---|---|---|---|---|---|
| Groups | Level[1] % | $C_2^2$ | $C_3^2$ | $C_4^2$ | Total VFA |
| I | Control | 1.00[3] | 1.05 | 1.07 | 1.00 |
| II | 0.05 | 0.97 | 1.06 | 1.11 | 0.88 |
| III | 0.075 | 0.92 | 1.24 | 1.05 | 0.89 |
| IV | 0.025 | 0.97 | 1.00 | 1.20 | 1.05 |

[1]Level is reported as percent of compound added to the total feed administered to the animal. A dose level of 0.05 percent corresponds approximately to 60 ppm of compound in the rumen.
[2]$C_2$ represents acetate, $C_3$ represents propionate and $C_4$ represents butyrate.
[3]Average of all values for biweekly samples taken over the 90-day trial period.

As illustrated by the results of these trials, the compounds of the present invention were found to be effective in decreasing the acetate concentration and correspondingly increasing the propionate production in the rumen of the animals for a sustained time period.

Testing of other compounds within the scope of this invention gives results that correspond to those set out in Tables II and III. It was also discovered that combining the compounds of the present invention with known rumen metabolic regulators, e.g., polyether antibiotics (monensin, etc.) resulted in a still further increase in propionate production with a concomitant decrease by both acetate and butyrate. Therefore, mixtures of two or more compounds of the present invention as feed additives, as well as mixtures of compounds of the present invention with known rumen metabolic regulators are within the scope of this invention.

It has been found that the compounds of the present invention improve the efficiency of feed utilization in ruminant animals when they are administered orally to the animals. The simplest and easiest manner to orally administer the compounds of this invention to the animals is by admixture to their feed. Any appropriate feed material for ruminant animals may be used including the concentrate feed previously described as well as roughage feeds such as silage or various commercial grain mixtures commonly used for ruminant animals.

The compounds of the present invention can be added to any conventional premix formulation, animal feed carriers or adjuvants in an amount sufficient to increase the efficiency of feed utilization by ruminant animals. In addition to the compounds of the present invention, the animal feed compositions may contain such additives as vitamins; minerals; natural oils; e.g., vegetable oil, animal fat, fish oils, etc.; antioxidants; antibiotics; anthelmintics; and other appropriate medicaments.

The compounds of the present invention may also be administered to the animals in other ways. For example, their may be incorporated into tablets, drenches, boluses, or capsules, and dosed to the animals in formulations and by means well known in the veterinary pharmaceutical art. They can also be administered in the field by means of salt or molasses blocks. Use of the compounds of the present invention for improving the efficiency of feed utilization of monogastric animals which digest at least a portion of their food by cereal and/or colon fermentation, since it follows a chemical pathway similar to rumen fermentation, is also contemplated by this invention.

In general, the scope of the present invention is not to be limited by any specific method of administration or any particular formulation of the compounds of this invention. Any manner or form for increasing the efficiency of feed utilization by ruminant animals by use of the compounds of the present invention is within the scope of this invention.

Other features and aspects of this invention will be appreciated by those skilled in the art upon reading and comprehending this disclosure. Such features, aspects and expected variations and modifications of the reported results are clearly within the scope of this invention where the invention is limited solely by the scope of the following claims.

What is claimed is:

1. An animal feed composition for increasing the efficiency of feed utilization by ruminant animals comprising an animal feed containing a feedstuff additive and an effective amount of at least one compound defined by one of the following formulae:

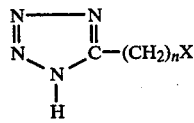

I.

where X represents Cl, Br,

$NHSO_2CH_3$,

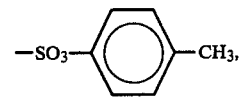

or $-SCH_3$, and n is 1 or 2; and $$CH_3SO_2NHCH_2CH_2CN \qquad (II)$$

to increase the efficiency of food utilization by the animal.

2. A composition according to claim 1 wherein the compound is:

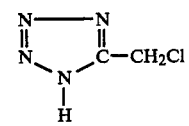

3. A composition according to claim 1 wherein the compound is:

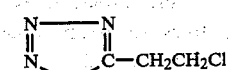

4. A composition according to claim 1 wherein the compound is:

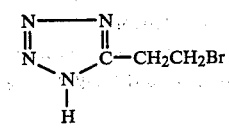

5. A composition according to claim 1 wherein the compound is:

$$CH_3SO_2NHCH_2CH_2CN$$

6. A composition according to claim 1 wherein the compound is:

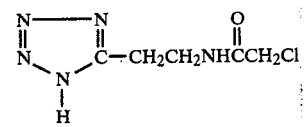

7. A composition according to claim 1 wherein the compound is:

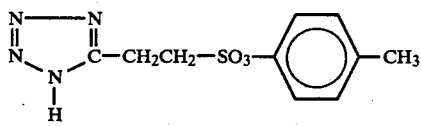

8. An animal feed composition comprising an animal feed containing at least one compound defined by one of the following formulae:

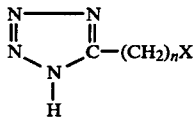   I.

where X represents Cl, Br,

NHSO$_2$CH$_3$,

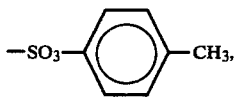

or —SCH$_3$, and n is 1 or 2; and

CH$_3$SO$_2$NHCH$_2$CH$_2$CN          (II)

in an amount sufficient to effect an increase in propionate production during food digestion to increase the efficiency of food utilization by the animal.

9. The feed composition according to claim 8 wherein the compound is present in an amount of from about 0.01 percent to 0.1 percent by weight of the total feed composition.

10. The feed composition of claim 9 wherein the compound is present in an amount of about 0.05 percent by weight of the total feed composition.

11. The feed compositions according to claim 8, 9 or 10 wherein the compound is selected from the group consisting of:

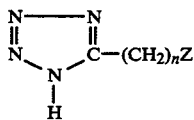   A.

where n is 1 or 2 and Z represents Cl, Br,

NHSO$_2$CH$_3$, or

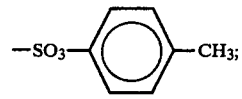

and CH$_3$SO$_2$NHCH$_2$CH$_2$CN;
or mixtures thereof.

12. The composition as defined in claim 8 wherein the composition contains an additional feed additive which is a polyether antibiotic.

13. The composition as defined in claim 12 wherein the additional feed additive is monensin.

14. A method for increasing the efficiency of feed utilization by ruminant animals having a developed rumen function which comprises administering to the animal in an amount sufficient to effect the increase of propionate production during food digestion, a feed additive comprising at least one compound defined by one of the following formulae:

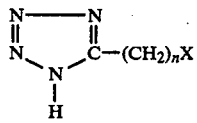   I.

where X represents Cl, Br,

NHSO$_2$CH$_3$,

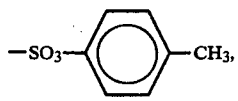

or —SCH$_3$, and n is 1 or 2; and

CH$_3$SO$_2$NHCH$_2$CH$_2$CN          (II)

15. A method according to claim 14 wherein the compound is administered orally by admixture to the animal's feed in an amount of from about 0.01 percent to 0.1 percent by weight of the total feed composition.

16. A method according to claim 15 wherein the compound is administered in an amount of about 0.05 percent by weight of the total feed composition.

17. A method according to claim 14, 15 or 16 wherein the animals are sheep.

18. A method according to claim 14, 15 or 16 wherein the animals are cattle.

19. A method according to claim 14, 15 or 16 wherein the compound is selected from the group consisting of:

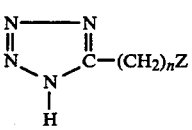

where n is 1 or 2 and Z represents Cl, Br,

—NHSO$_2$CH$_3$, or
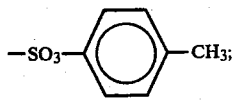
and CH$_3$SO$_2$NHCH$_2$CH$_2$CN; or mixtures thereof.
20. A method according to claim 19 wherein the animals are sheep or cattle.
* * * * *